United States Patent [19]

Adger et al.

[11] Patent Number: 6,140,512
[45] Date of Patent: Oct. 31, 2000

[54] PROCESS FOR THE PRODUCTION OF LIPOIC ACID

[75] Inventors: Brian Michael Adger; Raymond McCague, both of Cambridge; Stanley Michael Roberts, Liverpool, all of United Kingdom

[73] Assignee: ASTA Medica Aktiengesellschaft, Germany

[21] Appl. No.: 08/952,698

[22] PCT Filed: May 30, 1996

[86] PCT No.: PCT/GB96/01278

§ 371 Date: May 12, 1999

§ 102(e) Date: May 12, 1999

[87] PCT Pub. No.: WO96/38437

PCT Pub. Date: Dec. 5, 1996

[30] Foreign Application Priority Data

May 30, 1995 [GB] United Kingdom .................. 9510858

[51] Int. Cl.[7] .................................................. C07D 341/00
[52] U.S. Cl. ............................. 549/39; 554/125; 554/148
[58] Field of Search ..................... 549/266, 39; 554/125, 554/148

[56] References Cited

U.S. PATENT DOCUMENTS 5,489,694  2/1996  Paust et al. ................................ 549/39

*Primary Examiner*—Amelia Owens
*Attorney, Agent, or Firm*—Pillsbury Madison & Sutro LLP

[57] ABSTRACT

A process for the preparation of lipolic acid (thioctic acid), or a derivative thereof, is one in which a 2-substituted cyclohexanone is transformed in an oxidation reaction to a lactone having formula (I), wherein X is a heteroatom substituent.

5 Claims, No Drawings

PROCESS FOR THE PRODUCTION OF LIPOIC ACID

This application is the national phase of international application PCT/GB96/01278, filed May 30, 1996 which designated the U.S.

FIELD OF THE INVENTION

The present invention relates to a novel process for obtaining lipoic acid (thioctic acid) either in racemic or single enantiomer form, and intermediates in that process.

BACKGROUND TO THE INVENTION

Lipoic acid (thioctic acid) has been reported to have utility for a wide range of therapeutic applications, including liver disease and poisoning (see DE-A-4338508), hypertension (see DE-A-4343647), pain and infection, especially retroviral infection such as HIV (see EP-A-0427247). It has been reported that (R)-lipoic acid is preferred for conditions associated with diabetes such as polyneuropathy and nephropathy (see DE-A-4343593), and for treating chronic degenerative diseases of the central nervous system (CNS) (see DE-A-4343592). Whereas in EP-A-0572922, it has been reported that a combination of the unnatural (S)-enantiomer and vitamin E provides effective analgesia. Thus, synthetic routes to single enantiomer lipoic acid have been sought.

There are already various synthetic approaches reported, such as in Y. S. Yadav et al, J. Sci. Ind. Rev., (1990) 49: 400–409; P. C. Bullman Page et al, J. Chem. Soc. Perkin Trans. 1, (1990), 1615–18; B. R. Menon et al, Tetrahedron Lett., (1987) 28: 2183–6; S. A. Gopalan and J. H. Jacobs, J. Chem. Soc. Perkin Trans. 1, (1990), 1897–1900; J. D. Elliot et al, Tetrahedron Lett., (1985) 26: 2535–8; M. H. Brookes et al, J. Chem. Soc. Chem. Commun., (1983), 1051–3; and L. G. Chebotareva, Zhim.-Farm. Zh.,(1980) 14: 92–9, including classical resolution; asymmetric epoxidation of an intermediate; enantiomeric control by a chiral auxiliary; or derivation from an available chirality pool material. The existing routes are generally not ideal as they involve many steps, use expensive reagents or starting materials, or result in loss of half the desired material following resolution of a racemate. As a result there is a continuing need for a more economical synthetic route.

SUMMARY OF THE INVENTION

According to a first aspect of the present invention, a process for preparing lipoic acid (thioctic acid), or a derivative thereof, is one in which a 2-substituted cyclohexanone is transformed in an oxidation reaction to a lactone having the formula (2), below, wherein X is a heteroatom substituent and the lactone is converted to lipoic acid.

According to a second aspect of the present invention, a novel lactone has the formula (2), below, wherein X is a heteroatom substituent, and is in substantially single enantiomer form. By substantially single enantiomer we mean typically at least 50% ee, preferably at least 80% ee, more preferably at least 90% ee, or higher. Lactones of this type are particularly useful as intermediates in the preparation of single enantiomer lipoic acid.

DESCRIPTION OF THE INVENTION

One synthetic route to single enantiomer lipoic acid (or for that matter the racemate) embodied by the present invention starts with the very readily available starting material cyclohexanone and is outlined in Scheme 1 below. It is characterised by a Baeyer Villiger oxidation of a 2-substituted cyclohexanone.

In Scheme 1, X is generally a heteroatom substituent, such as an oxygen-containing substituent, e.g. —OH, -Oacyl, —OCOR (in which R is generally $C_{1-20}$ alkyl, but can be other groups), or a halogen atom.

Benefits of such a route are that (i) the starting material is inexpensive, as there are various ways to achieve substitution at the 2-position of cyclohexanone; and (ii) if the 2-substituted cyclohexanone is obtained in single enantiomer form through resolution, the incorrect enantiomer can be racemised (by virtue of the acidity of the proton at the stereogenic centre), and recycled into the resolution.

The resolution can be conducted by a variety of methods, such as by esterase bio-resolution where X is chosen to provide an 0-acyl derivative and kinetic resolution with an asymmetric Baeyer Villiger reaction, as is the case described below using a monooxygenase, or by fractional crystallisation if X is an ester (—O—COR) with a chiral acid which forms a crystalline ester. The Baeyer Villiger oxidation step to the lactone can be either biocatalytic or chemical with a per-acid.

An alternative to resolution of the 2-substituted cyclohexanone is to prepare it from a prochiral substrate by asymmetric synthesis, such as by formation of the enamine of cyclohexanone with a chiral amine and alkylation of that enamine with ethylene oxide (see W. E. Harvey and D. S. Tarbell, J. Org. Chem., (1967) 32: 1679–81; A. Z. Britten et al, Tetrahedron, (1969) 25: 3157–60; S. B. Zeinalov, Dokl. Akad. Nauk Az. SSR, (1985) 41: 45–7), or an equivalent thereof such as 2-iodoethyl acetate. Once obtained, a given enantiomer of the lactone (2) can be converted into either enantiomer of the final lipoic acid product, as illustrated in Scheme 2, below.

Scheme 2 shows an alternative synthetic route, differing from Scheme 1 in that there is a hydroxyl inversion in this particular sequence. This circumvents the need for a Mitsunobu inversion, thereby reducing the overall process to lipoic acid by two steps as compared to Scheme 1. An NADPH-dependent monooxygenase derived from *Pseudomonas putida* NCIMB 10007, termed "MO-2" (described in R. Gagnon et al, J. Chem. Soc. Perkin Trans. 1, (1994), 2537), has been found to effect a kinetic resolution of the 2-substituted cyclohexanone (3a) through converting one of its enantiomers into the lactone (2a) and leaving the other enantiomer of the ketone unconverted. Initial biocatalytic conversion has given the lactone (2a) in 83% ee and 34% yield while the remaining starting material (3a) has been obtained in 75% ee and 13% yield. (A subsequent experiment gave the lactone in 78% ee and 43% yield). The lactone (2a) has been trasesterified to (R)-methyl 6,8-dihydroxyhexanoate in 80% yield. Inversion by the Mitsunobu reaction and hydrolysis has given the corresponding (S)-ester, which has been converted by standard steps into (R)-(+)-lipoic acid having $[\alpha]_D$ 104° (c=1, benzene) compared with a literature value (see P. C. B. Page et al, J. Chem. Soc. Perkin. Trans. 1, (1990), 1615) of $[\alpha]_D$+107° (c=0.88, benzene).

Alternatively, by omitting the hydroxyl inversion steps from the reaction sequence in Scheme 2, (S)-lipoic acid may be synthesised.

The present invention is further illustrated by the following examples.

EXAMPLES

Example 1

Synthesis of (R)-lipoic acid via MO2 biotranformation and Mitsunobu inversion (±)-6-(Ethoxycarbonylmethyl)-1,4-dioxaspiro[4.5]decane Under an argon atmosphere, ethylene glycol (7.6 ml, 135.87 mmol) and para-toluenesulfonic acid (516 mg, 2.72 mmol) were added to a solution of (±)-2-(ethoxycarbonylmethyl)cyclohexanone (5.00 g, 27.17 mmol) in toluene (136 ml). The mixture was heated to reflux in a Dean Stark apparatus for 4 h and then allowed to cool to room temperature and quenched with sodium bicarbonate (5 g) and a saturated sodium bicarbonate solution (150 ml). The organic phase was separated from the aqueous phase which was extracted with ethyl acetate (3×100 ml). The combined organic phases were washed with a saturated sodium bicarbonate solution (100 ml) and brine (100 ml). The organic phase was dried over magnesium sulphate and the solvent was evaporated under reduced pressure to give the crude product which was purified using flash column chromatography with hexane-ethyl acetate (9:1) to give (±)-6-(ethoxycarbonylmethyl)-1,4-dioxaspiro[4.5]decane (4.59 g, 74% yield) as a colourless oil. $R_f$ 0.18 (hexane-ethyl acetate, 9:1).

(±)-6-(2'-Hydroxyethyl)-1,4-dioxaspiro[4.5]decane

Under an argon atmosphere, a solution of (±)-6-(ethoxycarbonylmethyl)-1,4-dioxaspiro[4.5]decane (1.00 g, 4.39 mmol) in diethyl ether (22 ml) was cooled to 0° C. Lithium aluminium hydride (333 mg, 8.77 mmol) was added and the mixture was stirred at room temperature for 3 h. The mixture was cooled to 0° C., quenched with ethyl acetate (10 ml) and 2 M sodium hydroxide solution (50 ml). The mixture was extracted with chloroform (3×50 ml) and the combined organic extracts were dried over magnesium sulphate. The solvent was evaporated under reduced pressure to give the crude product which was purified using flash column chromatography with hexane-ethyl acetate (3:7) to give (±)-6-(2'-hydroxyethyl)-1,4-dioxaspiro[4.5]decane (767 mg, 94% yield) as a colourless oil. $R_f$ 0.30 (hexane-ethyl acetate, 3:7).

(±)-2-(2'-Acetoxyethyl)cyclohexanone.

Under an argon atmosphere, DMAP (259 mg, 2.12 mmol) and acetic anhydride (3 ml, 31.75 mmol) were added to a solution of (±)-6-(2'-hydroxyethyl)-1,4-dioxaspiro [4.5] decane (3.94 g, 21.17 mmol) in pyridine (106 ml). The mixture was stirred at room temperature for 1 h. The pyridine was evaporated under reduced pressure and the residue was diluted with methanol (100 ml). The mixture was cooled to 0° C. and 2 M hydrochloric acid (250 ml) was added. The mixture was stirred at room temperature for 1 h and then extracted with chloroform (3×200 ml). The combined organic extracts were washed with 2 M hydrochloric acid (200 ml) and brine (300 ml). The organic phase was dried over magnesium sulphate and the solvent was evaporated under reduced pressure to give the crude product which was purified using flash column chromatography with hexane-ethyl acetate (3:1) to give (±)-2-(2'acetoxyethyl) cyclohexanone (3.45 g, 88% yield) as a colourless oil. $R_f$ 0.34 (hexane-ethyl acetate, 7:3).

Biotransformation of (±)-2-(2'-acetoxyethyl)cyclohexanone using MO-2 isolated from (1R)-(+)-camphor grown *Pseudomonas putida* NCIMB 10007

A solution of (±)-2-(2'-acetoxyethyl)cyclohexanone (660 mg, 3.59 mmol) in ethanol (3 ml) was added to a solution of MO-2 (partially purified by dialysis) in TRIZMA buffer (330 ml) containing NADPH tetrasodium salt (0.3 mmol) glucose-6-phosphate monosodium salt (282 mg, 3 mmol) and glucose-6-phosphate dehydrogenase (600 IU, from *Leuconostoc mesenteroides*). After incubation for 3 h at 30° C., the mixture was extracted with ethyl acetate (3×200 ml), and the combined organic extracts were washed with brine (200 ml), dried over magnesium sulphate, and concentrated under reduced pressure. The residue was purified by flash column chromatography with hexane-ethyl acetate (gradient 25–60–100% of ethyl acetate), once the products were isolated in the following order:

(2S)-(+)-2-(2'-Acetoxyethyl)cyclohexanone was isolated as a colourless oil (19% (GC), 88 mg, 13% yield]. $R_f$ 0.34 (hexane-ethyl acetate, 7:3).

(7R)-(−)-7-(2'-Acetoxyethyl) -2-oxepanone was isolated as a colourless oil [36% (GC), 241 mg, 34% yield]. $R_f$ 0.40 (hexane-ethyl acetate, 7:3).

(6R)-(+)-Methyl 6,8-dihydroxyoctanoate

Under an argon atmosphere, sodium methoxide (12 mg, 0.24 mmol) was added to a solution of (7R)-(−)-7-(2'-acetoxyethyl)-2-oxepanone (241 mg, 1.21 mmol) in methanol (12 ml) at room temperature. The mixture was stirred at room temperature for 3 h, quenched with a saturated ammonium chloride solution (40 ml) and extracted with chloroform (3×40 ml). The combined organic extracts were washed with brine (40 ml) and dried over magnesium sulphate. The solvent was evaporated under reduced pressure to give the crude product which was purified by flash column chromatography using ethyl acetate as eluent to give (6R)-(−) -methyl 6,8-dihydroxyoctanoate (184 mg, 80% yield) as a colourless oil. $R_f$ 0.30 (ethyl acetate, 100%).

(6S)-(+)-Methyl 6,8-bis(4-nitrobenzoxy)octanoate

Under an argon atmosphere, triphenylphosphine (1.016 g, 3.87 mmol) and 4-nitrobenzoic acid (647 mg, 3.87 mmol) were added to a solution of (6R)-(+)-methyl 6,8-dihydroxyoctanoate (184 mg, 0.97 mmol) in THF (9.7 ml). DEAD (0.6 ml, 3.87 mmol) was added dropwise over 15 min to the stirred mixture at room temperature. The mixture was stirred at room temperature for 30 min. The solvent was evaporated under reduced pressure and the residue was purified using flash column chromatography with hexane-ethyl acetate (3:1) to give (6S)-(+)-methyl 6,8-bis(4-nitrobenzoxy)octanoate (461 mg, 97% yield) as a clear yellow oil. $R_f$ 0.24 (hexane-ethyl acetate, 7:3).

(6S)-(−)-Methyl 6,8-dihydroxyoctanoate

Under an argon atmosphere, anhydrous potassium carbonate (130 mg, 0.94 mmol) was added to a solution of (6S)-(−)-methyl 6,8-bis(4-nitrobenzoxy)octanoate (461 mg, 0.94 mmol) in methanol (9.4 ml). The mixture was stirred at room temperature for 1 h and quenched with a saturated ammonium chloride solution (50 ml). The mixture was extracted with chloroform (3×50 ml) and the combined organic extracts were washed with brine (50 ml). The organic phase was dried over magnesium sulphate and the solvent was evaporated under reduced pressure to give the crude product which was purified using flash column chromatography with ethyl acetate to give (6S)-(−)-methyl 6,8-dihydroxyoctanoate (147 mg, 82% yield) as a colourless oil. $R_f$ 0.30 (ethyl acetate, 100%).

(6S)-(+) -Methyl 6.8-bis(methylsulfonyloxy)octanoate

Under an argon atmosphere, triethylamine (324 ml, 2.32 mmol) and methanesulfonyl chloride (132 ml, 1.70 mmol) were added to a solution of (6S)-(−)-methyl 6,8dihydroxyoctanoate (147 mg, 0.77 mmol) in dichloromethane (3.9 ml) at 0° C. The mixture was stirred at 0° C. for 30 min, then quenched with ice water (10 ml) and extracted with dichloromethane (10 ml). The extract was washed with 2 M hydrochloric acid (10 ml), saturated sodium bicarbonate solution (10 ml) and brine (10 ml). The organic phase was dried over magnesium sulphate and the solvent was evaporated under reduced pressure to give the crude product which was purified using flash column chromatography with hexane-ethyl acetate (2:3) to give (6S)-(+)-methyl 6,8-bis(methylsulfonyloxy)octanoate (247 mg, 92% yield) as a clear yellow oil. $R_f$ 0.30 (hexane-ethyl acetate, 3:2).

(R)-(+)-Methyl lipoate.

Under an argon atmosphere, finely grounded sodium sulphide nonahydrate (189 mg, 0.79 mmol) and sulphur (25 mg, 0.79 mmol) were dissolved in DMF (14 ml). The mixture was heated to 80° C. in the dark for 1 h. A solution of (6S)-(+)-methyl 6,8-bis(methylsulfonyloxy)octanoate (247 mg, 0.71 mmol) in DMF (2 ml) was added dropwise to the mixture at 80° C. over 25 min. The mixture was stirred at 80° C. for 2 h in the dark, cooled to room temperature and diluted with water (70 ml). The mixture was extracted with hexane (2×100 ml) and ethyl acetate (2×100 ml). The combined organic extracts were washed with brine (150 ml) and dried over magnesium sulphate. The solvent was evaporated to give the crude product which was purified using flash column chromatography with hexane-ethyl acetate (4:1) to give (R)-(+)-methyl lipoate (130 mg, 83% yield) as a clear yellow oil. $R_f$ 0.30 (hexane-ethyl acetate, 4:1)

(R)-(+)-Lipoic acid.

Potassium hydroxide (99 mg, 1.77 mmol) was dissolved in water (17.7 ml) and added to a solution of (R)-(+)-methyl lipoate (130 mg, 0.59 mmol) in methanol (17.7 ml). The mixture was stirred at room temperature for 3 h and then washed with chloroform (20 ml) to remove the organic impurities. The aqueous phase was acidified with 2 M hydrochloric acid (50 ml) and extracted with diethyl ether (3×50 ml). The combined organic extracts were washed with brine (50 ml) and dried over magnesium sulphate. The solvent was evaporated under reduced pressure to give the crude product which was recrystallized from hexane to give (R)-(+)-lipoic acid (85 mg, 70% yield) as yellow needles.

Example 2

Synthesis of racemic lipoic acid via non-enzymatic Baeyer Villiger oxidation (±)-7-(2'-Acetoxyethyl)-2-oxepanone Under an argon atmosphere, sodium bicarbonate (1.78 g, 21.20 mmol) and 80–90% w/w MCPBA (4.95 g, 28.26 mmol) were added to a solution of (±)-2-(2'-acetoxyethyl) cyclohexanone (2.60 g, 14.13 mmol) (0.50 mmol) in dichloromethane (70 ml) at room temperature. The mixture was stirred at room temperature for 3 h, and diluted with dichloromethane (80 ml) and washed sequentially with a saturated sodium sulphite solution (3×100 ml), distilled water (100 ml) and brine (100 ml). The organic phase was dried over magnesium sulphate. After filtration, the solvent was evaporated under reduced pressure to give the crude product which was purified by flash column chromatography using hexane-ethyl acetate (2:3) as eluent to give (±)-7-(2'-acetoxyethyl)-2-oxepanone, as a colourless oil (2.76 g, 98% yield). $R_f$ 0.40 (hexane-ethyl acetate, 7:3).

(±)-Methyl 6,8-dihydroxyoctanoate

Following the general procedure for transesterification (see Example 1), (±)-7-(2'-acetoxyethyl)-2-oxepanone (2.76 g, 13.80 mmol) was converted to (±)-methyl 6,8-dihydroxyoctanoate which was isolated after work-up and flash column chromatography with ethyl acetate as a colourless oil (2.57 g, 98% yield). $R_f$ 0.30 (ethyl acetate, 100%).

(±)-Methyl 6,8-bis(methylsulfonyloxyloctanoate

Under an argon atmosphere, triethylamine (0.7 ml, 5.05 mmol) and methanesulfonyl chloride (0.3 ml, 3.71 mmol) were added to a solution of (±)-methyl 6,8-dihydroxyoctanoate (320 mg, 1.68 mmol) in dichloromethane (8.4 ml) at 0° C. The mixture was stirred at 0° C. for 30 min, then quenched with ice water (20 ml) and extracted with dichloromethane (20 ml). The organic extract was washed with 2 M hydrochloric acid (20 ml), saturated sodium bicarbonate solution (20 ml) and brine (20 ml). The organic phase was dried over magnesium sulphate and the solvent was evaporated under reduced pressure to give the crude product which was purified using flash column chromatography with hexane-ethyl acetate (2:3) to give (±)-methyl 6,8-bis(methylsulfonyloxy)octanoate (581 mg, 99% yield) as a clear yellow oil. $R_f$ 0.30 (hexane-ethyl acetate, 3:2).

(±)-Methyl lipoate

Under an argon atmosphere, finely grounded sodium sulphide nonahydrate (17 mg, 0.54 mmol) and sulphur (10 mg, 0.54 mmol) were dissolved in DMF (8 ml). The mixture was heated to 80° C. in the dark for 1 h. A solution of (±)-methyl 6,8-bis(methylsulfonyloxy) octanoate (171 mg, 0.49 mmol) in DMF (2 ml) was added dropwise to the mixture at 80° C. over 15 min. The mixture was stirred at 80° C. for 2 h in the dark. It was then allowed to cool to room temperature and quenched with water (150 ml). The mixture was extracted with hexane (3×150 ml) and the combined organic extracts were washed with brine (150 ml). The organic phase was dried over magnesium sulphate and the solvent was evaporated to give the crude product which was purified using flash column chromatography with hexane-ethyl acetate (4:1) to give (±)-methyl lipoate (59 mg, 54% yield) as a clear yellow oil. $R_f$ 0.30 (hexane-ethyl acetate, 4:1).

(±)-Lipoic acid

Potassium hydroxide (24 mg, 0.42 mmol) was dissolved in water (4.2 ml) and added to a solution of (±)-methyl lipoate (28 mg, 0.13 mmol) in methanol (10 ml). The mixture was stirred at room temperature for 3 h and then washed with chloroform (10 ml) to remove the organic impurities. The aqueous phase was acidified with 2 M hydrochloric acid (15 ml) and extracted with diethyl ether (3×20 ml). The combined organic extracts were washed with brine (20 ml) and dried over magnesium sulphate. The solvent was evaporated under reduced pressure to give the crude (±)-lipoic acid (26 mg, 98% yield) as yellow needles.

Example 3

Alternative biotransformation of (±)-2-(2'-acetoxyethyl) cyclohexanone, giving (S)-lactone:

Preparative scale biotransformation of (±)-2-(2'-acetoxyethyl)cyclohexanone using cyclopentanone monooxygenase (CPMO) isolated from cyclopentanol grown Pseudomonas sp. NCIMB 9872.

NADPH (91 mg, 0.11 mmol) and (±)-2-(2'-acetoxyethyl) cyclohexanone (20 mg, 0.11 mmol) were added to a solution of cyclopentanone monooxygenase (3.12 IU) in Trisma buffer (20 ml, 50 mM, pH 7.5). The mixture was agitated in an orbital incubator (200 rpm, 30° C.) for 45 min and then extracted with ethyl acetate (3×20 ml). The combined organic extracts were washed with brine (20 ml) and dried over magnesium sulphate. The solvent was evaporated under reduced pressure to give the crude product. Purification using flash column chromatography with hexane-ethyl acetate (gradient 25–60% of ethyl acetate) afforded the following products:

(2R)-(−)-2-(2'-Acetoxyethyl)cyclohexanone was the first product eluted and isolated as a colourless oil [38% (GC), 7 mg, 37% yield]. $R_f$ 0.34 (hexane-ethyl acetate, 7:3). (7S)-(+)-7-(2'-Acetoxyethyl)-2-oxepanone was the second product eluted and isolated as a colourless oil (62% (GC), 13 mg, 59% yield). $R_f$ 0.40 (hexane-ethyl acetate, 7:3).

(6S)-(−)Methyl 6,8-dihydroxoctanoate

Under an argon atmosphere, sodium methoxide (3 mg, 0.06 mmol) was added to a solution of (7S)-(+)-7-(2'-acetoxyethyl)-2-oxepanone (13 mg, 0.06 mmol) in methanol (0.6 ml) at room temperature. The mixture was stirred at room temperature for 3 h, quenched with a saturated ammonium chloride solution (5 ml) and extracted with chloroform (3×5 ml). The combined extracts were washed with brine (5 ml) and dried over magnesium sulphate. The solvent was evaporated under reduced pressure to give the crude product which was purified by flash column chromatography using ethyl acetate as eluent to give (6S)-(−)-methyl 6,8-dihydroxyoctanoate (8 mg, 63% yield) as a colourless oil. $R_f$ 0.30 (ethyl acetate, 100%).

Scheme 1

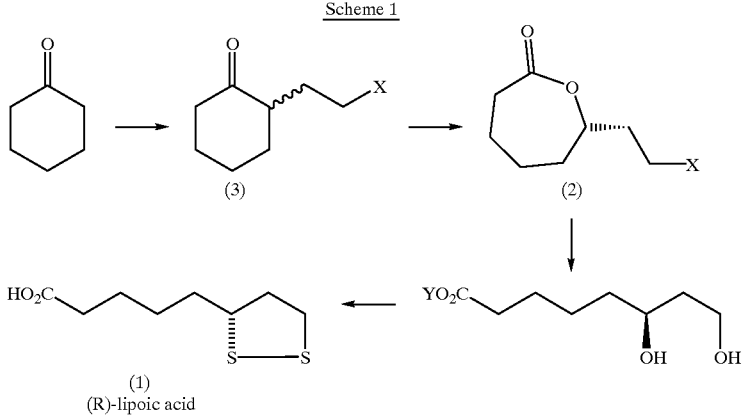

(1) (R)-lipoic acid

Scheme 2

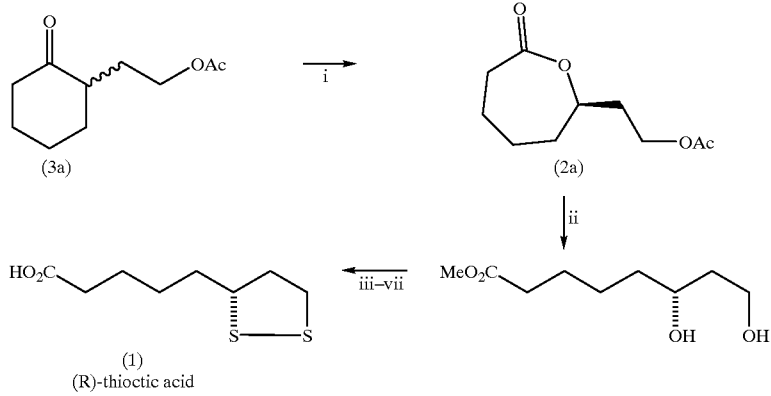

(1) (R)-thioctic acid

Reagents: i, microbial strain MO-2; ii, NaOMe, MeOH; iii, p-O$_2$N.C$_6$H$_4$.CO$_2$H, PPh$_3$, DEAD, THF; iv, K$_2$CO$_3$, MeOH; v, MsCl, NEt$_3$, CH$_2$Cl$_2$; vi, Na$_2$S.9H$_2$O, S, DMF; vii, KOH, MeOH.

What is claimed is:

1. A process for the production of (6S)-(−) methyl-6,8-dihydroxyoctanoate, in which a lactone having the formula

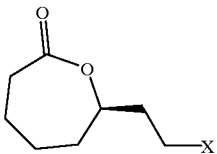

wherein X is a heteroatom substituent, is reacted with sodium methoxide.

2. A process for the production of (6R)-(+) methyl-6,8-dihydroxyoctanoate, in which a lactone having the formula

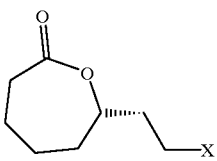

wherein X is a heteroatom substituent, is reacted with sodium methoxide.

3. A process for the production of (±) methyl-6,8-dihydroxyoctanoate, in which a lactone having the formula

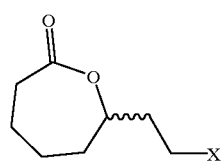

wherein X is a heteroatom substituent, is reacted with sodium methoxide.

4. A process for the preparation of a substantially single enantiomer of lipoic acid or a derivative thereof, having either (R) or (S) symmetry, comprising the steps of:

oxidizing a 2-substituted cyclohexanone to obtain a substantially single enantiomer of a lactone of formula I having either (R) or (S) symmetry

I

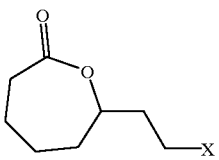

wherein X is a heteroatom substituent; and converting the lactone into the lipoic acid or derivative thereof, said process comprising the steps of:

a) transesterifying the (R)-lactone of formula I with sodium methoxide to give a substantially (R) methyl ester;

b) inverting the substantially (R) methyl ester via a Mitsunobu reaction;

c) hydrolysis to afford a substantially (S) methyl ester; and d) converting the (S) methyl ester into the substantially single enantiomer of the (R) lipoic acid.

5. A process for the preparation of a substantially single enantiomer of lipoic acid or a derivative thereof, having either (R) or (S) symmetry, comprising the steps of:

oxidizing a 2-substituted cyclohexanone to obtain a substantially single enantiomer of a lactone of formula I having either (R) or (S) symmetry

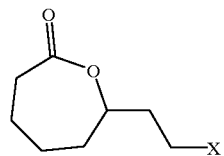

I wherein X is a heteroatom substituent; and converting the lactone into the lipoic acid or derivative thereof, said process comprising the steps of:

a) transesterifing the (R) lactone of formula I with sodium methoxide to afford a substantially (R) methyl ester; and b) converting the (R) methyl ester into the substantially single enantiomer of (S) lipoic acid.

* * * * *